United States Patent
Akiba

(10) Patent No.: US 10,905,323 B2
(45) Date of Patent: Feb. 2, 2021

(54) BLOOD FLOW MEASUREMENT APPARATUS

(71) Applicant: KABUSHIKI KAISHA TOPCON, Tokyo (JP)

(72) Inventor: Masahiro Akiba, Toda (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 0 days.

(21) Appl. No.: 15/536,359

(22) PCT Filed: Nov. 2, 2015

(86) PCT No.: PCT/JP2015/080968
§ 371 (c)(1),
(2) Date: Jun. 15, 2017

(87) PCT Pub. No.: WO2016/098472
PCT Pub. Date: Jun. 23, 2016

(65) Prior Publication Data
US 2017/0347879 A1     Dec. 7, 2017

(30) Foreign Application Priority Data

Dec. 19, 2014 (JP) .................. 2014-257032

(51) Int. Cl.
*A61B 3/12* (2006.01)
*A61B 5/026* (2006.01)
(Continued)

(52) U.S. Cl.
CPC .............. *A61B 3/12* (2013.01); *A61B 3/0025* (2013.01); *A61B 3/102* (2013.01); *A61B 5/0066* (2013.01); *A61B 5/0261* (2013.01); *G01N 21/17* (2013.01)

(58) Field of Classification Search
CPC ......... A61B 3/12; A61B 3/102; A61B 5/0066; G01N 21/17
(Continued)

(56) References Cited

U.S. PATENT DOCUMENTS 9,492,082 B2 * 11/2016 Yoshida ............... A61B 5/0066
2009/0005691 A1 1/2009 Huang et al.
(Continued)

FOREIGN PATENT DOCUMENTS

JP   2004-290408 A   10/2004
JP   2009-165710 A    7/2009
(Continued)

OTHER PUBLICATIONS

International Search Report and Written Opinion dated Feb. 9, 2016, in connection with International Patent Application No. PCT/JP2015/080968, 6 pgs.
(Continued)

*Primary Examiner* — Pascal M Bui Pho
*Assistant Examiner* — Marjan Saboktakin
(74) *Attorney, Agent, or Firm* — Chiesa Shahinian & Giantomasi PC

(57) ABSTRACT

A scanner of a blood flow measurement apparatus of an embodiment alternately performs first scan and second scan for first and second cross sections both intersecting an interested blood vessel. An image forming unit forms one or more images of the first cross section including a phase image of the first cross section and an image of the second cross section. A blood vessel region specification unit specifies a first blood vessel region in any of the one or more images of the first cross section and a second blood vessel region in the image of the second cross section. A gradient calculation unit calculates a gradient of the interested blood vessel at the first cross section based on the first and second
(Continued)

blood vessel regions. A blood flow information generation unit generates blood flow information based on the phase image and the gradient.

12 Claims, 8 Drawing Sheets

(51) Int. Cl.
  *A61B 3/00* (2006.01)
  *G01N 21/17* (2006.01)
  *A61B 3/10* (2006.01)
  *A61B 5/00* (2006.01)

(58) Field of Classification Search
  USPC .......................................................... 600/425
  See application file for complete search history.

(56) References Cited

U.S. PATENT DOCUMENTS

| 2011/0178395 A1* | 7/2011 | Miesner ............. A61B 1/00041 |
| | | 600/425 |
| 2015/0313466 A1 | 11/2015 | Yoshida |
| 2016/0302738 A1 | 10/2016 | Yoshida et al. |
| 2016/0310024 A1 | 10/2016 | Yoshida et al. |

FOREIGN PATENT DOCUMENTS

| JP | 2010-523286 A | 7/2010 |
| JP | 2013-184018 A | 9/2013 |
| JP | 2013-202298 A | 10/2013 |

OTHER PUBLICATIONS

Notification of Reasons for Refusal dated Sep. 25, 2018, in connection with Japanese Patent Application No. 2015-186246, 7 pgs.

* cited by examiner

BLOOD FLOW MEASUREMENT APPARATUS

CROSS-REFERENCE TO RELATED APPLICATIONS

This application is a national stage (under 35 U.S.C. 371) of International Patent Application No. PCT/JP2015/080968, filed Nov. 2, 2015, claiming priority to Japanese Patent Application No. 2014-257032, filed Dec. 19, 2014, both of which are herein incorporated by reference in their entirety.

TECHNICAL FIELD

Embodiments described herein relate generally to a blood flow measurement apparatus.

BACKGROUND

Optical coherence tomography (OCT) is utilized not only for morphology measurement of an object but also for function measurement. For example, OCT apparatuses for blood flow measurement of living bodies are known. The blood flow measurement using OCT is applied to blood vessels of the eye fundus.

SUMMARY

In general, the acquisition of the blood flow information using OCT requires the estimation of the orientation of the blood vessel to be measured. This is because the blood flow information is determined based on the Doppler frequency shift that varies according to the angle between the blood flow direction (i.e., the orientation of the blood vessel) and the incident direction of the measurement light on the living body. According to conventional blood flow measurement techniques, the blood flow information is acquired by individually performing the measurement for estimating the blood vessel orientation and Doppler OCT, by applying Doppler OCT to two cross sections, or the like.

However, such conventional techniques have a disadvantage of prolonging measurement time. For example, since the blood flow information is collected over a period equal to or longer than a period of one heartbeat, Doppler OCT is performed over a sufficient period for this collection (e.g., 2 seconds). Accordingly, when the measurement for estimating the blood vessel orientation and Doppler OCT are performed separately, the time for the former measurement and the time for Doppler OCT are both required. On the other hand, when Doppler OCT is applied to two cross sections, Doppler OCT must be performed twice.

If the object can move as in the case in which the object is a living eye, the movement of the object may occur during a period between the measurement for estimating the blood vessel orientation and Doppler OCT or between the two Doppler OCT measurements, which deteriorates the reliability of the blood flow information determined.

The purpose of embodiments is to shorten the measurement time and to improve the reliability.

A blood flow measurement apparatus of an embodiment includes the followings: a scanner configured to alternately perform first scan that scans a first cross section that intersects an interested blood vessel of a living body and second scan that scans a second cross section that intersects the interested blood vessel using optical coherence tomography; an image forming unit configured to form one or more images of the first cross section including a phase image that represents chronological change in phase difference in the first cross section based on data acquired through the first scan, and form an image of the second cross section based on data acquired through the second scan; a blood vessel region specification unit configured to specify a first blood vessel region corresponding to the interested blood vessel in any of the one or more images of the first cross section, and specify a second blood vessel region corresponding to the interested blood vessel in the image of the second cross section; a gradient calculation unit configured to calculate a gradient of the interested blood vessel at the first cross section based on the first blood vessel region and the second blood vessel region; and a blood flow information generation unit configured to generate blood flow information on the interested blood vessel based on the phase image and the gradient of the interested blood vessel.

According to the embodiment, the measurement time can be shortened and the reliability can be improved.

DETAILED DESCRIPTION

Figure 1:
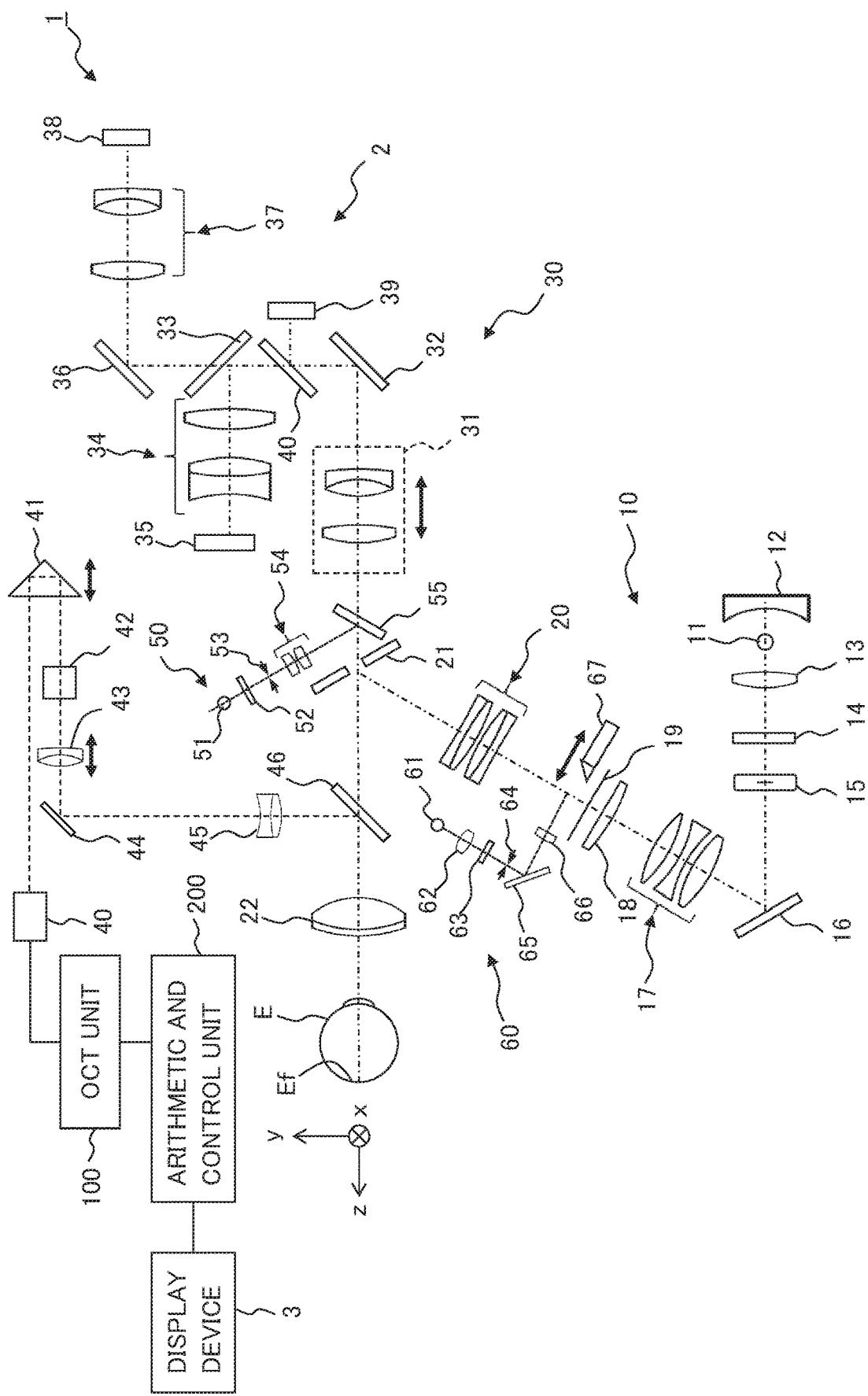
FIG. 1 is a schematic diagram illustrating an example of the configuration of the blood flow measurement apparatus according to the embodiment.

Exemplary embodiments of the present invention will be described in detail with referring to the drawings. Any of the contents of the documents cited in the present specification may be applied to the embodiments below.

A blood flow measurement apparatus of an embodiment acquires information on the blood flow of a living body using OCT. The blood flow measurement apparatus is capable of acquiring images of the living body using OCT. Described below is the case in which Fourier domain OCT (in particular, spectral domain OCT) is utilized to perform the blood flow measurement for eye fundus. The object of blood flow measurement is not necessarily eye fundus. The object of blood flow measurement may be any biological tissue such as skin or internal organs. The type of OCT is not limited to spectral domain OCT. Any type of OCT such as swept source OCT or time domain OCT may be utilized. The embodiment below describes an apparatus that is a combination of an OCT apparatus and a fundus camera. Similar configurations to the embodiment below may be applied to other type such as an apparatus configured as a combination of an OCT apparatus and a slitlamp microscope, or a combination of an OCT apparatus and an ophthalmic operational microscope. Similar configurations to the embodiment below may also be applied to an apparatus having the OCT function only.

<Configuration>

As shown in FIG. 1, the blood flow measurement apparatus 1 includes the fundus camera unit 2, the OCT unit 100, and the arithmetic and control unit 200. The fundus camera unit 2 has a configuration for photographing the fundus Ef. The OCT unit 100 has a configuration for acquiring OCT images of the fundus Ef. The arithmetic and control unit 200 has a configuration for executing various kinds of calculation and control.

<Fundus Camera Unit>

The fundus camera unit 2 acquires two dimensional images rendering the surface morphology of the fundus Ef (referred to as fundus images). The kinds of the fundus images include observation images and photographed images. An observation image is a monochrome image acquired at a preset frame rate using near infrared light. The kinds of the photographed images include: color images captured using visible flash light; monochrome images captured using near infrared light or visible light (e.g., fluorescence images such as fluorescein angiograms, indocyanine green angiograms, autofluorescence images).

The fundus camera unit 2 includes the illumination optical system 10 and the photographing optical system 30. The illumination optical system 10 irradiates the eye E with illumination light. The photographing optical system 30 receives return light (e.g., fundus reflection light, cornea reflection light, fluorescence, etc.) of the illumination light from the eye E. The fundus camera unit 2 guides measurement light from the OCT unit 100 toward the eye E, and guides return light of the measurement light from the eye E to the OCT unit 100.

Light emitted from the observation light source 11 in the illumination optical system 10 (i.e., observation illumination light) is reflected by the reflection mirror 12 having the curved reflective surface, is refracted by the condenser lens 13, and passes through the visible light cut filter 14. Thereby, the observation illumination light becomes near infrared light. Then, the observation illumination light once converges at a point near the photographing light source 15, is reflected by the mirror 16, passes through the relay lenses 17 and 18, the diaphragm 19, and relay lens 20, is reflected by the peripheral area (that is, the area surrounding the aperture) of the aperture mirror 21, passes through the dichroic mirror 46, is refracted by the objective lens 22, and is projected onto the eye E.

Return light of the observation illumination light from the eye E is refracted by the objective lens 22, passes through the dichroic mirror 46, passes through the aperture formed in the central area of the aperture mirror 21, passes through the dichroic mirror 55, passes through the focusing lens 31, is reflected by the mirror 32, passes through the half mirror 40, is reflected by the dichroic mirror 33, and converges on the light receiving surface of the area sensor 35 with the condenser lens 34. The area sensor 35 detects the return light at a preset frame rate. With this, an observation image of the fundus Ef, an observation image of the anterior segment or the like is acquired.

Light emitted from the photographing light source 15 (i.e., photographing illumination light) is guided along the same route as that of the observation illumination light, and projected onto the eye E (that is, onto the fundus Ef). Return light (e.g., fundus reflection light, fluorescence, etc.) of the photographing illumination light is also guided along the same route as that of the observation illumination light until the dichroic mirror 33, passes through the dichroic mirror 33, is reflected by the mirror 36, and converges on the light receiving surface of the area sensor 38 with the condenser lens 37. With this, a photographed image of the fundus Ef or the like is acquired.

Liquid crystal display (LCD) 39 displays a fixation target, an optotype (visual acuity chart), and the like. Part of light output from the LCD 39 is reflected by the half mirror 40, is reflected by the mirror 32, passes through the focusing lens 31 and the dichroic mirror 55, passes through the aperture of the aperture mirror 21, passes through the dichroic mirror 46, is refracted by the objective lens 22, and is projected onto the eye (that is, onto the fundus Ef). The fixation position of the eye E is changed by changing the displayed position of the fixation target on the LCD 39.

The fundus camera unit 2 includes the alignment optical system 50 and the focus optical system 60. The alignment optical system 50 generates an indicator for position adjustment of the optical system of the apparatus with respect to the eye E. Such position adjustment is referred to as alignment, and the indicator for the alignment is referred to as the alignment indicator. The focus optical system 60 generates an indicator for focus adjustment with respect to the eye E. The indicator for the focus adjustment is referred to as the split indicator.

Near infrared light emitted from the light emitting diode (LED) 51 in the alignment optical system 50 (referred to as alignment light) passes through the diaphragms 52 and 53 and the relay lens 54, is reflected by the dichroic mirror 55, passes through the aperture of the aperture mirror 21, passes through the dichroic mirror 46, and is projected onto the eye E (i.e., the cornea) with the objective lens 22. Return light of the alignment light is guided along the same route as that of the return light of the observation illumination light, and detected by the area sensor 35. The image detected by the area sensor 35 (referred to as an alignment indicator image) is rendered in the observation image. The user or the arithmetic and control unit 200 can perform alignment based on the position of the alignment indicator image in the same manner as with conventional fundus cameras.

When performing focus adjustment, the reflective surface of the reflection rod 67 is placed in the optical path of the illumination optical system 10 in an inclined manner. Near infrared light emitted from the LED 61 in the focus optical system 60 (referred to as focus light) passes through the relay lens 62, is split into two light beams with the split indicator plate 63, passes through the two-aperture diaphragm 64, is reflected by the mirror 65, once converges on the reflective surface of the reflection rod 67 with the condenser lens 66, is reflected by the reflection rod 67, passes through the relay lens 20, is reflected by the aperture mirror 21, passes through the dichroic mirror 46, is refracted by the objective lens 22, and is projected onto the eye E (i.e., the fundus Ef). Return light of the focus light is guided along the same route as that of the return light of the alignment light, and detected by the area sensor 35. The image detected by the area sensor 35 (referred to as a split indicator image) is rendered in the observation image. The user or the arithmetic and control unit 200 can perform focus adjustment by moving the focusing lens 31 and the focus optical system 60 based on the position of the split indicator image in the same manner as with conventional fundus cameras.

Figure 3:
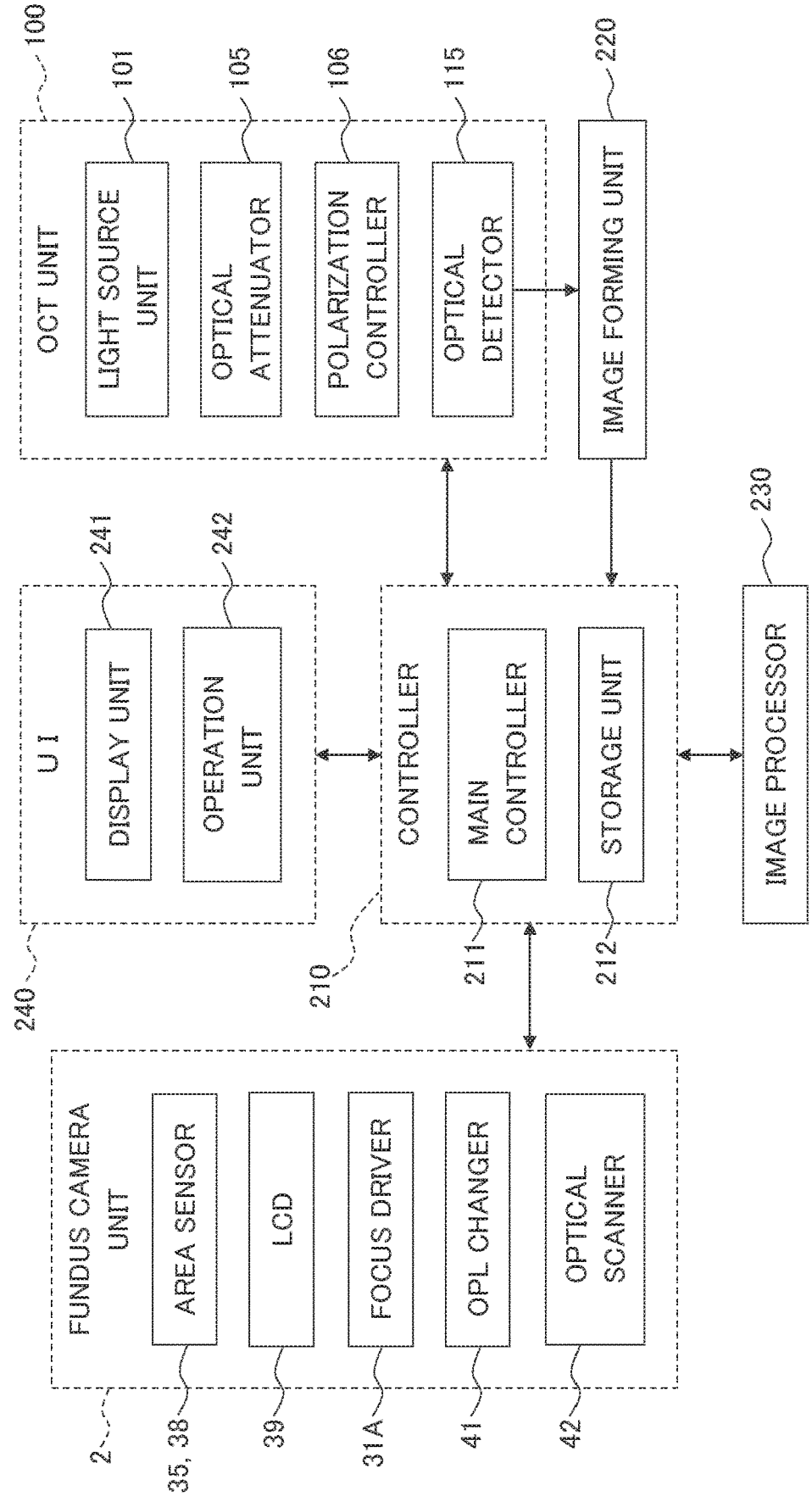
FIG. 3 is a schematic diagram illustrating an example of the configuration of the blood flow measurement apparatus according to the embodiment.

The focus driver 31A shown in FIG. 3 moves the focusing lens 31, and a driver mechanism (not illustrated) moves the focus optical system 60.

After the completion of alignment (and focus adjustment), tracking may be performed. Tracking is an operation for moving the optical system of the apparatus in accordance with the movement of the eye E.

The dichroic mirror 46 couples the optical path for fundus photography and the optical path for OCT together. The optical path for OCT is referred to as a measurement arm, sample arm, or the like. The dichroic mirror is designed to reflect light of wavelength bands for OCT and to transmit light for fundus photography. Listed from the OCT unit 100 side, the collimator lens unit 40, the optical path length (OPL) changer 41, the optical scanner 42, the focusing lens 43, the mirror 44, and the relay lens 45 are placed in the optical path for OCT.

The optical path length changer 41 changes the length of the measurement arm. The optical path length changer 41 includes, for example, a corner cube movable in the direction shown by the arrow in the FIG. 1. Change of the optical path length of the measurement arm may be utilized for the adjustment of the optical path length according to the axial length of the eye E, the adjustment of the interference state, or the like.

The optical scanner 42 has a configuration capable of two-dimensionally deflecting light guided along the measurement arm (i.e., the measurement light LS). In an example, the optical scanner 42 is configured to be capable of deflecting the measurement light LS in mutually orthogonal directions (e.g., the x direction and the y direction). With such a configuration, various types of scan patterns can be realized. When a configuration for anterior segment OCT (e.g., an attachment including a lens system) is employed, the anterior segment of the eye E is scanned with the measurement light LS. The optical scanner 42 includes, for example, a Galvano mirror, micro electro mechanical systems (MEMS) mirror, resonant mirror, or the like.

<OCT Unit>

Figure 2:
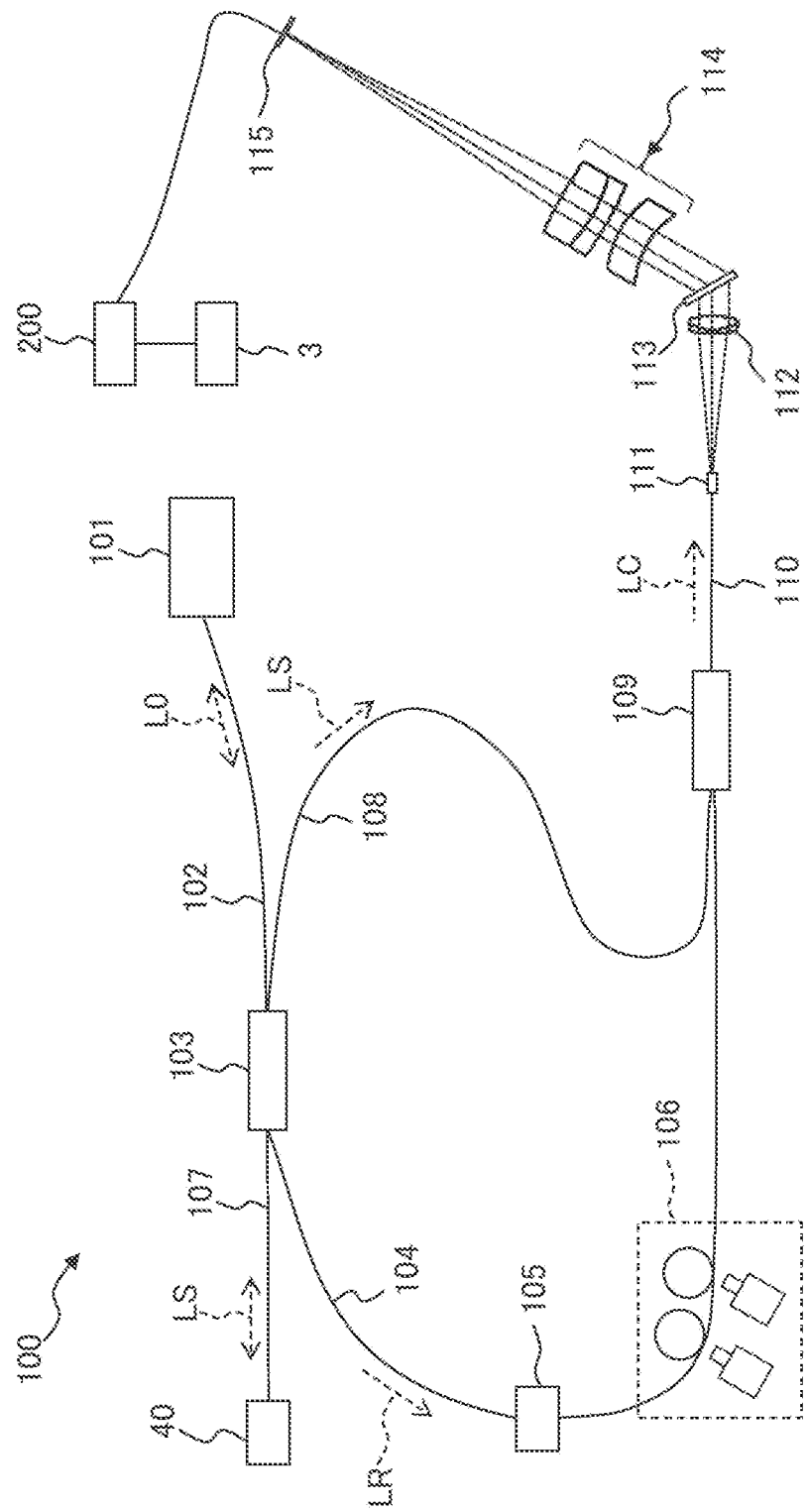
FIG. 2 is a schematic diagram illustrating an example of the configuration of the blood flow measurement apparatus according to the embodiment.

FIG. 2 shows a configuration example of the OCT unit 100. The configuration of the OCT unit 100 depends on the type of OCT applied. The configuration shown in FIG. 2 is an example for spectral domain OCT. The spectral domain OCT system, in general, includes a low coherence light source and a spectrometer. On the other hand, the swept source OCT system includes, for example, a wavelength tunable light source and a balanced photo diode.

In the spectral domain OCT system, the light L0 emitted from the light source unit 101 is broadband, low coherence light. In an example, the light L0 may include near infrared wavelength bands (e.g., about 800 nm to 900 nm), and the temporal coherence length of the light L0 may be about several tens μm. Alternatively, the light L0 may be near infrared light having the central wavelength of about 1040 nm to 1060 nm. The light source unit 101 includes a light emitting device such as a super luminescent diode (SLD), an LED, or a semiconductor optical amplifier (SOA).

The light L0 output from the light source unit 101 is guided to the fiber coupler 103 through the optical fiber 102, and is split into the measurement light LS and the reference light LR.

The reference light LR is guided to the optical attenuator 105 through the optical fiber 104. Under the control of the arithmetic and control unit 200, the optical attenuator 105 automatically adjusts the amount of the reference light LR guided through the optical fiber 104 as with conventional techniques. The reference light LR, the amount of which has been adjusted by the optical attenuator 105, is guided to the polarization controller 106 through the optical fiber 104. Under the control of the arithmetic and control unit 200, the polarization controller 106 controls the polarization state of the reference light LR guided through the optical fiber 104 as with conventional techniques. The reference light LR, the polarization state of which has been adjusted, is guided to the fiber coupler 109.

The measurement light LS generated by the fiber coupler 103 is guided through the optical fiber 107, and is converted to a parallel light beam with the collimator lens unit 40. Then, the measurement light LS passes through the optical path length changer 41, the optical scanner 42, the focusing lens 43, the mirror 44, and the relay lens 45, is reflected by the dichroic mirror 46, is refracted by the objective lens 22, and is projected onto the eye E (that is, onto the fundus Ef). The measurement light LS is scattered and reflected at various depth positions of the fundus Ef. Return light of the measurement light LS (e.g., backscattering light, reflection light, fluorescence) travels along the same route as the outward way in the opposite direction, is guided to the fiber coupler 103, and is guided to the fiber coupler 109 through the optical fiber 108. The focusing lens 43 is moved by a focus driver (not illustrated).

The fiber coupler 109 superposes the return light of the measurement light LS and the reference light LR that has traveled through the optical fiber 104. Interference light LC thus generated is guided through the optical fiber 110, exits from the exit end 111 of the optical fiber 110, is converted to a parallel light beam with the collimator lens 112, is split into spectra with the diffraction grating 113, converges with the condenser lens 114, and is projected on the light receiving surface of the optical detector 115. The optical detector 115 is, for example, a line sensor, and detects the respective spectral components of the interference light LC split into spectra and generates an electric signal (that is, a detection signal). The detection signal generated is sent to the arithmetic and control unit 200.

<Arithmetic and Control Unit>

The arithmetic and control unit 200 executes control of the fundus camera 2, the display device 3, and the OCT unit 100, various kinds of calculation processing, formation of OCT images, etc. The arithmetic and control unit 200 includes a user interface such as a display device, an input device, an operation device. The description of the configuration of the arithmetic and control unit 200 will be given in the description of the control system below.

<Control System>

Figure 4:
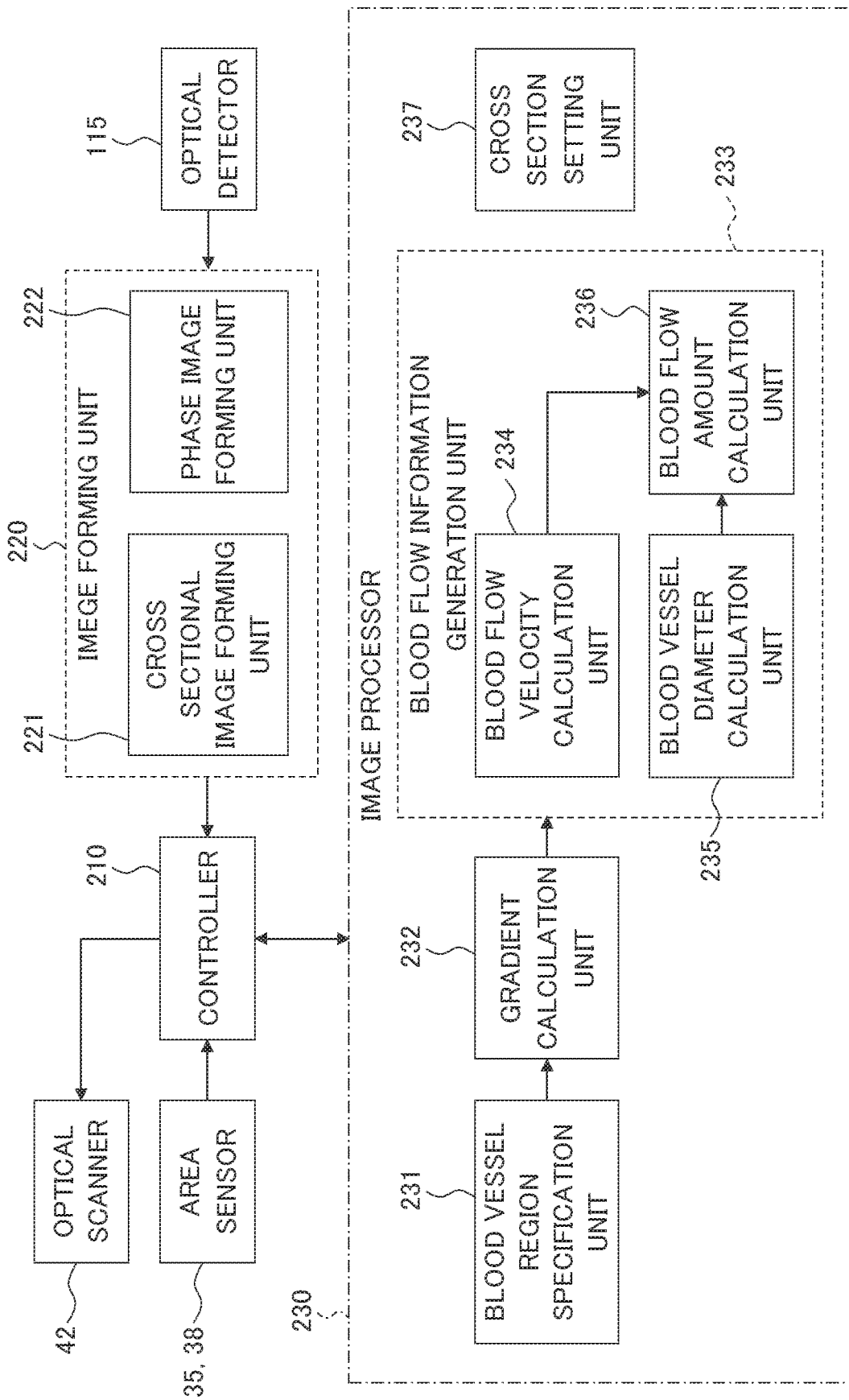
FIG. 4 is a schematic diagram illustrating an example of the configuration of the blood flow measurement apparatus according to the embodiment.

The control system of the blood flow measurement apparatus 1 will be described with referring to FIGS. 3 and 4.

(Controller)

The controller 210 is the center of the control system of the blood flow measurement apparatus 1. The controller 210 includes the main controller 211 and the storage unit 212.

(Main Controller)

The main controller 211 executes control of the fundus camera 2, the OCT unit 100, and the arithmetic and control unit 200. The main controller 211 stores data in the storage unit 212 and reads out data from the storage unit 212.

(Storage Unit)

The storage unit 212 stores various kinds of data. Examples of data stored in the storage unit 212 include, for example, OCT images, fundus images, and subject's eye information. The subject's eye information is information on subject's eyes and/or subjects, and includes input information such as patient IDs, medical information such as electronic medical records, or the like. The storage unit 212 stores computer programs and data for operating the blood flow measurement apparatus 1.

(Image Forming Unit)

The image forming unit 220 forms image data of a cross sectional image and image data of a phase image based on detection signals from the optical detector 115. The image data will be described later. Sometimes, the present specification does not makes no distinction between "image data" and an "image" created based on the image data. The image forming unit 220 includes the cross sectional image forming unit 221 and the phase image forming unit 222.

Figure 5:
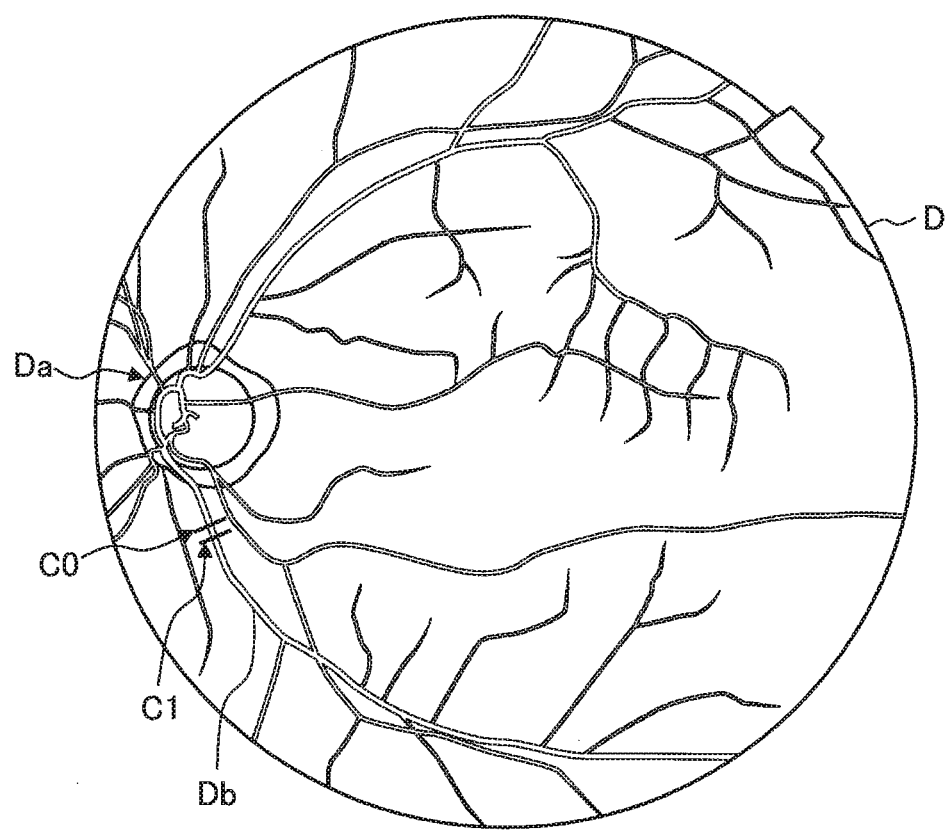
FIG. 5 is a schematic diagram illustrating an example of the configuration of the blood flow measurement apparatus according to the embodiment.

In the present embodiment, two different kinds of scans (first scan and second scan) are applied to the fundus Ef. In the first scan, a first cross section that intersects a predetermined interested blood vessel of the fundus Ef is repeatedly scanned with the measurement light LS. In the second scan, a second cross section that intersects the interested blood vessel is scanned with the measurement light LS. The second cross section is set near the first cross section. It may be desirable that the first cross section and the second cross section are oriented in such a manner that they are orthogonal to the running direction of the interested blood vessel. It may be desirable that the first cross section and the second cross section are set in such a manner that they are parallel to one another. FIG. 5 shows a specific example of the first cross section and the second cross section. On the fundus image D shown in FIG. 5, the first cross section C0 and the second cross section C1 are illustrate. The first cross section C0 and the second cross section C1 are set near the optic nerve head Da of the fundus Ef. The first cross section C0 and the second cross section C1 are set in such a manner that both of them intersect the predetermined interested blood vessel Db. The second cross section C1 may be set more on upstream side of the interested blood vessel Db than the first cross section C0, or may be set more on downstream side.

It may be desirable that the first cross section and the second cross section are performed during a period equal to or longer than one heartbeat (i.e., one pulsation cycle, or cardiac cycle) of the heart of the patient. With this, blood flow information is acquired for all time phases of the cardiac cycle. The execution period of the first scan may be a preset period with a constant length, or may be set for each patient or each examination. In the former case, a period longer than general cardiac cycle (e.g., 2 seconds) can be set. The latter case is executed with referring to examination data such as an electro cardiogram of the patient. Any factors other than the cardiac cycle may be considered. Examples of the factors include examination time (i.e., burden on the patient), response time of the optical scanner 42 (i.e., scan intervals), and response time of the optical detector 115 (i.e., scan intervals).

(Cross Sectional Image Forming Unit)

The cross sectional image forming unit 221 forms a cross sectional image (referred to as a first cross sectional image) that represents chronological change in morphology in the first cross section based on detection results of the interference light LC acquired through the first scan. This image formation will be described more in detail. As mentioned above, the first scan is iterative scan of the first cross section C0. During the first scan, detection signals are successively input from the optical detector 115 of the OCT unit 100 to the cross sectional image forming unit 221. Based on detection signals corresponding to each single scan of the first cross section C0, the cross sectional image forming unit 221 forms a single cross sectional image in the first cross section C0. The cross sectional image forming unit 221 iterates such image formation as many times as the number of repetition of the first scan. Thereby, the cross sectional image forming unit 221 forms a series of cross sectional images arranged in time series order. The cross sectional image forming unit 221 may divide these cross sectional images into a plurality of groups and synthesize (e.g., average) cross sectional images in each group to improve image quality.

The cross sectional image forming unit 221 forms a cross sectional image (referred to as a second cross sectional image) that represents morphology in the second cross section C1 based on detection results of the interference light LC acquired through the second scan of the second cross section C1. This image formation is executed in the same manner as for the first cross sectional image. The second cross sectional image may be a single cross sectional image while the first cross sectional image is a series of cross sectional images arranged in time series order. The image quality of the second cross sectional image may be improved by scanning the second cross section C1 a plurality of times and by synthesizing (e.g., averaging) resulting cross sectional images.

Processing of forming such cross sectional images includes noise elimination (noise reduction), filtering, fast Fourier transform (FFT), and the like as in conventional spectral domain OCT techniques. When other type of OCT is applied, the cross sectional image forming unit 221 executes known processing according to the type of OCT.

(Phase Image Forming Unit)

The phase image forming unit 222 forms a phase image that represents chronological change in phase difference in the first cross section based on detection results of the interference light LC acquired through the first scan. The detection results processed here is the same as that processed in the formation of the first cross sectional image performed by the cross sectional image forming unit 221. Accordingly, position matching between the first cross sectional image and the phase image can be performed. That is, pixels in the first cross sectional image and those in the phase image can be associated with each other in a natural manner.

An example of the method of the formation of phase images will be described. A phase image in this example is obtained by calculating the phase differences between adjacent A-line complex signals (that is, signals corresponding to adjacent scan points). In other words, a phase image in this example is formed based on chronological change in the pixel value (brightness value) of each pixel in the first cross sectional image. For any pixel, the phase image forming unit 222 creates a graph of the chronological change in the brightness value of the concerned pixel. The phase image forming unit 222 determines the phase difference $\Delta\varphi$ between two time points t1 and t2 that are apart from each other by a preset time interval $\Delta t$ in the graph. Here, $t2=t1+\Delta t$. The phase difference $\Delta\varphi$ is defined as the phase difference $\Delta\varphi(t1)$ at the time point t1. More generally, the phase difference $\Delta\varphi$ may be defined as the phase difference at any time point between t1 and t2 (including t1 and t2). By executing such processing for each of a plurality of time points set in advance, the chronological change in the phase difference at the concerning pixel.

A phase image is formed by representing, as an image, the values of the phase differences at the respective time points for the respective pixels. Such imaging processing can be realized by representing the values of the phase differences with colors. It is possible to assign different colors to a case where phase increases with the lapse of time and a case where it decreases. For example, red is assigned to the former case while blue is assigned to the latter case. It is also possible to represent the magnitude of the amount of change in phase with the density of display color. With such representation methods, the direction and/or magnitude of blood flow can be clearly represented with colors. The processing described here is applied to each pixel. Thereby, a phase image is formed.

The time interval Δt is set sufficiently small to secure phase correlation. This allows to obtain the chronological change in phase difference. Here, oversampling is executed in which the time interval Δt is set to be a value smaller than the period corresponding to the resolution of cross sectional images in the scan with the measurement light LS.

<Image Processor>

The image processor 230 applies various kinds of image processing, analysis, or the like to images formed by the image forming unit 220. For example, the image processor 230 executes various kinds of image correction such as brightness correction or dispersion correction. In addition, the image processor 230 applies various kinds of image processing, analysis, or the like to images (e.g., fundus images, anterior eye images) acquired by the fundus camera unit 2.

The image processor 230 includes the blood vessel region specification unit 231, the gradient calculation unit 232, and the blood flow information generation unit 233. The blood flow information generation unit 233 includes the blood flow velocity calculation unit 234, the blood vessel diameter calculation unit 235, and the blood flow amount calculation unit 236. In addition, the image processor 230 includes the cross section setting unit 237. These units 231 to 237 will be described below.

<Blood Vessel Region Specification Unit>

The blood vessel region specification unit 231 specifies a blood vessel region corresponding to the interested blood vessel Db for each of the first cross sectional image, the second cross sectional image, and the phase image. The specification can be executed by analyzing the pixel value of each pixel. This analysis may be thresholding.

Although the first cross sectional image and the second cross sectional image have enough resolution to apply the analysis, the phase image may not have enough resolution to specify the boundary (i.e., contour) of the blood vessel region. However, since the phase image is used for the generation of blood flow information, the blood vessel region in the phase image must be specified with high precision and high accuracy. On that account, the following processing can be employed to specify the blood vessel region in the phase image with higher accuracy.

As described above, the first cross sectional image and the phase image are formed based on the common detection signals, and the pixels of the first cross sectional image and those of the phase image can be associated in a natural manner. With this association, the blood vessel region specification unit 231 first analyzes the first cross sectional image to determine the blood vessel region in the first cross sectional image, and then determines the image region in the phase image consisting of the pixels corresponding to the pixels included in the blood vessel region in the first cross sectional image. The image region determined is regarded as the blood vessel region in the phase image. With such processing, the blood vessel region in the phase image can be specified with high precision and high accuracy.

<Gradient Calculation Unit>

Based on the distance between the first cross section and the second cross section (referred to as cross section interval) and the result of the specification of the blood vessel regions, the gradient calculation unit 232 calculates the gradient (or, inclination or tilt) of the interested blood vessel Db at the first cross section. The cross section interval is set in advance, and an example of which will be described later in the description of the cross section setting unit 237.

The gradient of the interested blood vessel Db is calculated for the following reason. The blood flow information is obtained by using Doppler OCT technique. The velocity component of blood flow contributing to Doppler shift is the component in the projection direction of the measurement light LS. Therefore, even when the blood flow velocity is the same, Doppler shift given to the measurement light LS changes according to the angle between the blood flow direction (i.e., the gradient of the interested blood vessel) and the projection direction of the measurement light LS. Thereby, the blood flow information acquired is also changed. In order to avoid such a problem, it is necessary to determine the gradient of the interested blood vessel Db and perform the calculation of the blood flow velocity based on the gradient.

Figure 6:
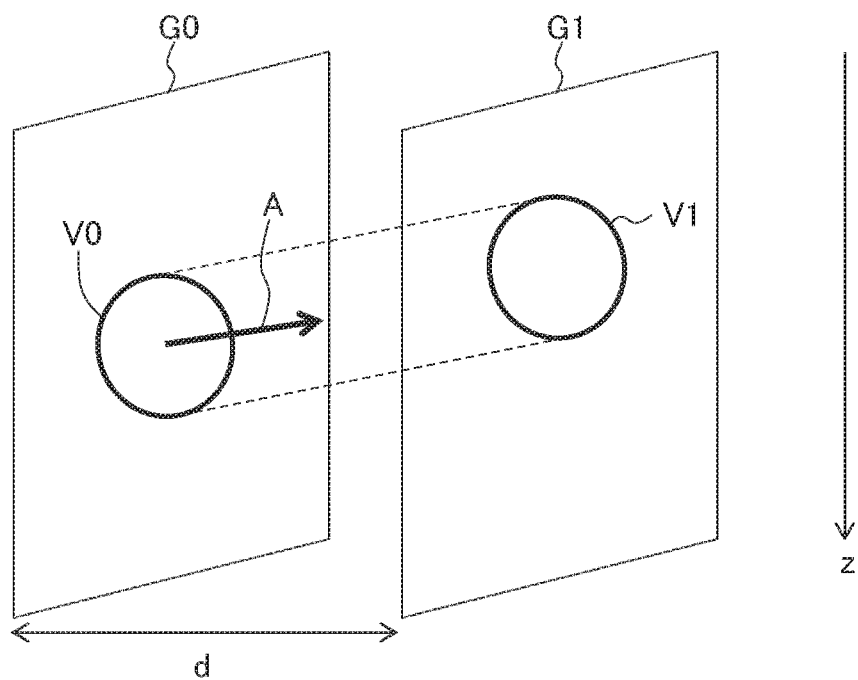
FIG. 6 is a schematic diagram illustrating an example of the configuration of the blood flow measurement apparatus according to the embodiment.

A method of calculating the gradient of the interested blood vessel Db will be described with referring to FIG. 6. The symbol G0 indicates the first cross sectional image of the first cross section C0, and the symbol G1 indicates the second cross sectional image of the second cross section C1. The symbol V0 indicates the blood vessel region in the first cross sectional image G0, and the symbol V1 indicates the blood vessel region in the second cross sectional image G1. In FIG. 6, the z coordinate axis is oriented downward, and substantially coincides with the projection direction of the measurement light LS. Further, the cross section interval is indicated by "d".

The gradient calculation unit 232 calculates the gradient "A" of the interested blood vessel Db at the first cross section C0 based on the positional relationship between the two blood vessel regions V0 and V1. The positional relationship is obtained, for example, by connecting the two blood vessel regions V0 and V1. More specifically, the gradient calculation unit 232 specifies a representative point in the blood vessel region V0 and a representative point in the blood vessel region V1, and connects the two representative points with a line segment. The representative point may be the center position, the position of the center of gravity, the highest position (the position corresponding to the smallest z coordinate value), the lowest position (the position corresponding to the largest z coordinate value), or the like.

Further, the gradient calculation unit 232 calculates the gradient A based on the line segment connecting the two representative points. More specifically, the gradient calculation unit 232 calculates the gradient of the line segment connecting the representative point in the first cross section C0 and the representative point in the second cross section C1, and set the calculated value to be the gradient A. The cross section interval "d" is used, in the calculation of the line segment, to embed the two cross sectional images G0 and G1 in the xyz coordinate system.

In the present example, a single value is obtained for the gradient. However, two or more gradients corresponding to two or more positions in the blood flow region V0 may be obtained. In such a case, the obtained two or more gradient values may be used separately. Alternatively, it is possible to execute statistical calculation to obtain a single value (e.g., mean value) from the obtained two or more gradient values, and set the obtained single value to be the gradient A.

<Blood Flow Information Generation Unit>

The blood flow information generation unit 233 generates blood flow information on the interested blood vessel Db based on the phase image and the gradient of the interested blood vessel Db. The following is a description of a configuration example for executing the generation of the blood flow information. As mentioned above, the blood flow information generation unit 233 includes the blood flow velocity calculation unit 234, the blood vessel diameter calculation unit 235, and the blood flow amount calculation unit 236.

(Blood Flow Velocity Calculation Unit)

Based on the phase image (i.e., chronological change in phase difference) and the gradient A of the interested blood vessel Db, the blood flow velocity calculation unit 234 calculates the blood flow velocity at the first cross section C0 for the blood flowing through the interested blood vessel Db. The parameter to be calculated may be the blood flow velocity at a certain time point, or may be the chronological change in the blood flow velocity. The chronological change in the blood flow velocity is referred to as blood flow velocity variation information. When the blood flow velocity at a certain time point is determined, the blood flow velocity at a predetermined time phase in an electro cardiogram (e.g., time phase corresponding to R wave) may be selectively acquired. When the chronological change in the blood flow velocity is determined, the measurement period is the whole or an arbitrary part of the period taken for the scan of the first cross section C0.

When the blood flow velocity variation information is acquired, the blood flow velocity calculation unit 234 can further calculate a statistic of the blood flow velocity in the measurement period. Examples of the statistic include the mean value, the standard deviation, the variance, the median, the global maximum, the global minimum, the local maximum, and the local minimum. The blood flow velocity calculation unit 234 can also create a histogram on the blood flow velocity values.

The blood flow velocity calculation unit 234 calculates the blood flow velocity using Doppler OCT technique as described above. In the blood flow velocity calculation, the gradient A of the interested blood vessel Db at the first cross section C0 calculated by the gradient calculation unit 232 is taken into account. Specifically, the blood flow velocity calculation unit 234 applies the following formula to the blood flow velocity calculation.

$$\Delta f = \frac{2nv\cos\theta}{\lambda} \quad \text{(Formula 1)}$$

Here:

$\Delta f$ indicates the Doppler shift given to scattered light of the measurement light LS;

n indicates the refractive index of medium;

v indicates the flow velocity of the medium (blood flow velocity);

$\theta$ indicates the angle between projection direction of the measurement light LS and the flow vector of the medium; and $\lambda$ indicates the center wavelength of the measurement light LS.

In the present embodiment, n and $\lambda$ are known, $\Delta f$ is obtained from the chronological change of the phase difference, and $\theta$ is obtained from the gradient A (alternatively, $\theta$ is the gradient A). The blood flow velocity v is calculated by substituting these values into the above formula.

When the chronological changes in the parameters are taken into account, it can be expressed that the Doppler shift $\Delta f = \Delta f(t)$ and the angle $\theta = \theta(t)$. Here, t is a variable representing time. The blood flow velocity calculation unit 234 can use the following formula to determine[[d]] the blood flow velocity v(t) at an arbitrary time, or to determine the chronological changes in the blood flow velocity v(t).

$$\Delta f(t) = \frac{2nv(t)\cos\theta(t)}{\lambda} \quad \text{(Formula 2)}$$

(Blood Vessel Diameter Calculation Unit)

The blood vessel diameter calculation unit 235 calculates the diameter of the interested blood vessel Db at the first cross section C0. Examples of this calculation include a first calculation method that utilizes a fundus image and a second calculation method that utilizes a cross sectional image.

When applying the first calculation method, an area of the fundus Ef including the location of the first cross section C0 is photographed in advance. The fundus image thus obtained may be an observation image (e.g., a frame(s) thereof), or may be a photographed image. When the photographed image is a color image, any image obtained from the color image (e.g., a red-free image) may be used.

The blood vessel diameter calculation unit 235 sets a scale of the fundus image based on various kinds of factors that determines the relationship between the scale of images and the scale in the real space such as the photographing angle of view (photographing magnification), the working distance, information on eyeball optical system. The scale of the fundus image may represent length in the real space. As a specific example, the scale associates interval between adjacent pixels with the scale in the real space (e.g., pixel interval=10 μm). It is possible to determine, in advance, the relationship between various values of the above factors and the scale in the real space, and store a table or a graph that represents the determined relationship. In this case, the blood vessel diameter calculation unit 235 selects the scale corresponding to the above factors, and uses the selected scale.

Based on the scale and the pixels included in the blood vessel region V0, the blood vessel diameter calculation unit 235 calculates the diameter of the interested blood vessel Db at the first cross section C0, that is, the diameter of the blood vessel region V0. As a specific example, the blood vessel diameter calculation unit 235 may calculate the maximum or the mean value of a plurality of diameters of the blood vessel region V0 corresponding to different directions. The blood vessel diameter calculation unit 235 may determine an approximate circle or an approximate ellipse of the contour of the blood vessel region V0, and calculate the diameter of the approximate circle or the approximate ellipse. Note that once the blood vessel diameter of the blood vessel region V0 is determined, the area of the blood vessel region V0 can (substantially) be calculated. That is, it is possible to substantially associate the blood vessel diameter with the area in one-to-one fashion. Hence, the area can be calculated in place of the blood vessel diameter.

The second calculation method will be described. In the second calculation method, a cross sectional image of the fundus Ef at the first cross section C0 is used. The cross sectional image may be the first cross sectional image, the phase image, or any other image.

The scale of the cross sectional image is determined according to the scan mode of the measurement light LS. In the present embodiment, the first cross section C0 is scanned as shown in FIG. 5. The length of the first cross section C0 is determined based on various kinds of factors that define the relationship between the scale of an image and the scale in the real space such as the working distance, the information about eyeball optical system. The blood vessel diameter calculation unit 235, for example, determines the interval between adjacent pixels based on the length of the first cross section C0, and calculates the diameter of the interested blood vessel Db at the first cross section C0 in the same manner as in the first calculation method. The chronological change in the blood vessel diameter can also be determined.

(Blood Flow Amount Calculation Unit)

Based on the calculation result of the blood flow velocity and the calculation result of the blood vessel diameter, the blood flow amount calculation unit 236 calculates the flow amount (or, flow volume or flow rate) of the blood that flows through the interested blood vessel Db. An example of this processing will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is expressed as in the following formula.

$$Q = \frac{\pi w^2}{8} Vm \qquad \text{(Formula 3)}$$

The blood flow amount calculation unit 236 substitutes the blood vessel diameter w calculated by the blood vessel diameter calculation unit 235 and the maximum blood flow velocity Vm based on the blood flow velocity calculated by the blood flow velocity calculation unit 234 into this formula to determine the blood flow amount Q. In another example, the blood flow amount calculation unit 236 executes the time integration of the product (or the integrated value) of the chronological change of the blood flow velocity and the blood vessel diameter (or the chronological change thereof) to determine the blood flow amount Q. The unit of the blood flow amount Q is, for example, µL/min.

(Cross Section Setting Unit)

The main controller 211 displays a fundus image on the display unit 241. The fundus image may be an observation image or a photographed image. The fundus image may be any image that constitutes a photographed image. The user operates the operation unit 242 to designate the first cross section C0 in the displayed fundus image. Based on the designated first cross section C0 and the fundus image, the cross section setting unit 237 sets the second cross section C1. As mentioned above, the first cross section C0 is designated such that the first cross section C0 intersects the desired interested blood vessel Db.

For example, a pointing device is used to perform the operation of designating the first cross section C0 in the fundus image. When the display unit 241 is a touch panel, the user touches a desired location in the displayed fundus image to designate the first cross section C0. In this case, parameters (e.g., orientation, length) of the first cross section C0 is set manually or automatically.

When setting manually, for example, the user can use a predetermined interface to set the parameters. The interface may include hardware such as a switch, or may include software such as a graphical user interface (GUI).

When setting automatically, for example, the cross section setting unit 237 sets the parameters based on the location designated in the fundus image by the user. A predetermined value of the length may be automatically set. The length may be automatically set based on the designated location and the locations of blood vessels near the designated location. The predetermined value of the length is designated, for example, based on general distance between a predetermined interested blood vessel and blood vessels in the vicinity thereof. Information on the general distance may be generated based on clinical data. This is the same in the case in which the designated location and the locations of the nearby blood vessels. In either case, the length of the first cross section C0 is set so as to intersect the interested blood vessel Db and intersect no other blood vessels (in particular, thick blood vessels).

When automatically setting the orientation of the first cross section C0, a predetermined orientation may be set, or the orientation of the interested blood vessel Db may be taken into account. In the farmer case, information representing the gradients of a predetermined interested blood vessel at a plurality of locations is generated, and the information is used in the automatic setting. The information may be generated based on clinical data. In the latter case, the running direction of the interested blood vessel Db at a designated location is determined, and the orientation of the first cross section C0 is set based on the designated running direction. The designation of the running direction includes thinning of the interested blood vessel Db, for example. In either case, the orientation of the first cross section C0 may be set such that the first cross section C0 orthogonally intersects the running direction.

Next, the setting of the second cross section C1 will be described. The cross section setting unit 237 sets the second cross section C1 at a location that is predetermined distance away from the first cross section C0. The predetermined distance is set to 100 µm, for example. The specification of the predetermined distance is carried out in the aforementioned manner, for example. Further, the length and/or the orientation of the second cross section C1 may be set in the same way as for the first cross section C0.

In the present embodiment, the cross sections C0 and C1 (that is, the scan positions of the measurement light LS) are set based on a fundus image. To do so, the correspondence between positions in a fundus image and scan positions is required. In order to obtain the correspondence, it is preferable that, as in the present embodiment, part of the optical system for fundus photography and part of the optical system for OCT are common. With such a coaxial configuration, the common optical axis can be used as a reference to associate the positions in the fundus image with the scan positions. Here, the display magnification of the fundus image, which includes at least any one of so-called optical zooming and digital zooming) may be taken into account to obtain the correspondence.

When such a coaxial configuration is not applied, the positions in a fundus image and scan positions may be associated with each other based on the fundus image and a projection image formed by OCT. The projection image is an image that renders the morphology of the fundus Ef and is created by adding up, along the depth direction (z direction), a three dimensional image acquired through the three dimensional scan (i.e., through the raster scan). Using such a projection image, the positions in the fundus image and the positions in the projection image can be associated with each other by means of image correlation, for example. Such association gives the correspondence between the positions of the fundus image and the scan positions. When taking into account the influence of the eye movement of the eye E (e.g., involuntary eye movement during fixation), it can be thought that the coaxial configuration is more preferable because the acquisition of the fundus image and OCT can be performed with substantially no time lag.

The image processor 230 having the above functions includes, for example, a microprocessor, RAM, ROM, hard disk drive, circuit board, and the like. Computer programs for the microprocessor to execute the above functions are stored, in advance, in the storage device such as the hard disk drive.

(User Interface)

A user interface 240 includes the display unit 241 and the operation unit 242. The display unit 241 includes the aforementioned display device of the arithmetic and control unit 200, the display device 3, and the like. The operation unit 242 includes the aforementioned operation devices of the arithmetic and control unit 200. The operation unit 242 may also include various kinds of buttons, keys, etc. that are arranged on the housing of the blood flow measurement apparatus 1 or are peripheral equipment. For example, when the housing of the fundus camera unit 2 is similar to that of the conventional fundus camera, the operation unit 242 may include a joy stick, an operation panel, etc. arranged on the housing. The display unit 241 may include various kinds of display devices such as a touch panel monitor arranged on the housing of the fundus camera unit 2.

The display unit 241 and the operation unit 242 do not need to be individual devices. For example, like a touch panel, a device having both the display function and the operation function can be employed. In such a case, the operation unit 242 includes a touch panel and computer programs. Contents of operation performed using the operation unit 242 are input into the controller 210 as electrical signals. Further, operation and information input may be carried out using the GUI displayed on the display unit 241 and the operation unit 242.

<Operation>

Figure 7:
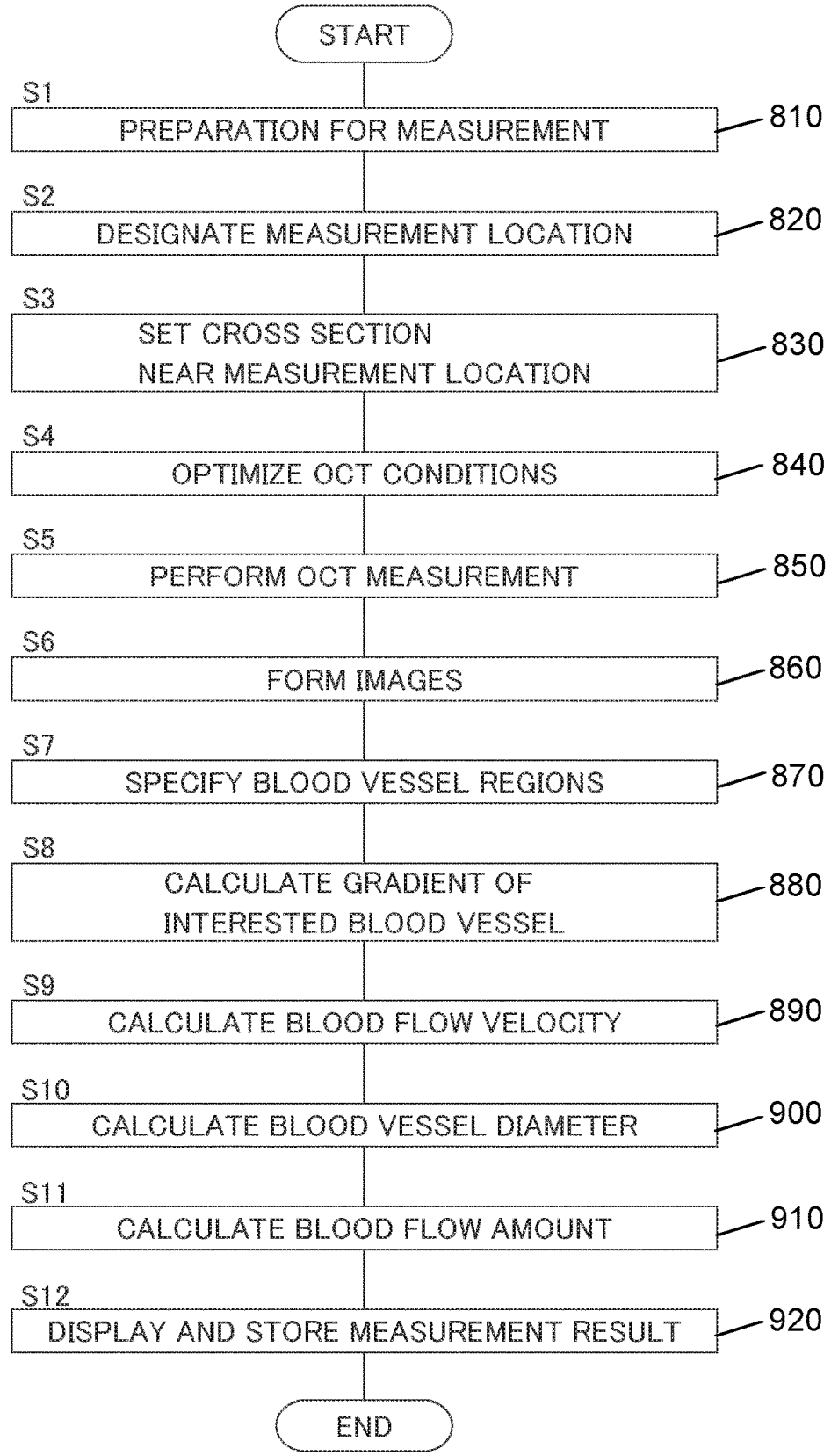
FIG. 7 is a flow chart illustrating an example of the operation of the blood flow measurement apparatus according to the embodiment.

The operation of the blood flow measurement apparatus 1 will be described. FIG. 7 shows an example of the operation of the blood flow measurement apparatus 1.

At step 810 (S1), the preparation for OCT includes the input of patient ID, the selection of an operation mode corresponding to the present embodiment (i.e., blood flow measurement mode), or the like. Subsequently, alignment and focus adjustment are performed. In addition, tracking may be commenced. Furthermore, a fundus image (e.g., an observation image, a photographed image, or an image constituting a photographed image) is displayed on the display unit 241.

Then, at step 820 (S2), the user designates the location where the blood flow is to be measured in the fundus image displayed. Here, the first cross section is designated. The method of designating the first cross section is described above. Alternatively, the first cross section may be automatically designated with referring to a predetermined site (e.g., optic nerve head) of the fundus Ef. Such automatic designation includes, for example, a process of specifying the predetermined site, a process of specifying the interested blood vessel, a process of setting the first cross section such that the first cross section is apart from the specified predetermined site by a predetermined distance and intersects the specified interested blood vessel. The series of processes is executed by the cross section setting unit 237.

Upon designating the first cross section in step 830 (S3), the cross section setting unit 237 sets the second cross section based on the first cross section.

The main controller 211 controls the light source unit 101, the optical scanner 42, etc. to perform preparatory OCT measurement. The preparatory OCT measurement in step 840 (S4) is applied to the first cross section, the second cross section, or another cross section. Then, it is determined whether an image acquired through the preparatory OCT measurement is adequate or not. The determination may be carried out through the visual observation by the user. Alternatively, the determination may be automatically executed by the blood flow measurement apparatus 1.

When determining through the visual observation, the main controller 211 displays the OCT image on the display unit 241. The user checks the image quality of the OCT image, the displayed location of a predetermined tissue (e.g., blood vessels, the surface of the retina) in the OCT image, or the like. When the OCT image is inadequate, the user adjusts measurement conditions. For example, when the displayed location is inadequate, the user operates the optical path length changer 41 to adjust the optical path length of the measurement light LS. When the image quality is inadequate, the user operates the optical attenuator 105, the polarization controller 106, or the like.

When the determination is automatically executed, the blood flow measurement apparatus 1 evaluates the image quality, the displayed location of the predetermined tissue, etc. with referring to a predetermined evaluation criterion, and adjusts the measurement conditions based on the result of the evaluation in the same manner as in the manual adjustment.

Figure 8:
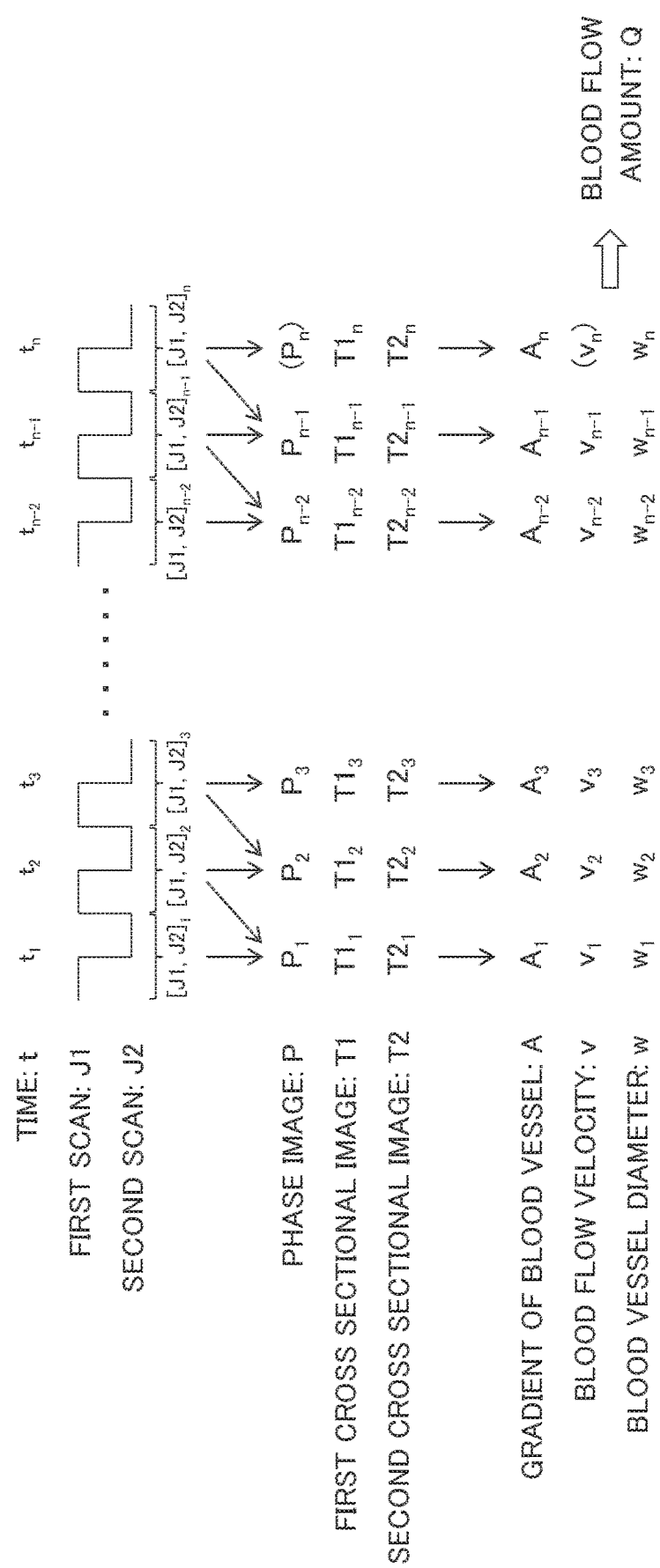
FIG. 8 is a schematic diagram illustrating an example of the configuration of the blood flow measurement apparatus according to the embodiment.

Upon receiving a predetermined trigger, the main controller 211 starts OCT measurement (i.e., blood flow measurement) at step 850 (S5). FIG. 8 shows an outline of the processes executed in the present operation example. During the OCT measurement of this step, it is to be desired that the tracking having been started in step 810 (S1) is continued. With this, substantially the same locations (the first cross section and the second cross section) can be scanned even when the eye E moves during the OCT measurement.

The present operation example alternately performs the first scan J1 and the second scan J2. The first scan J1 is the OCT measurement of the first cross section at which blood flow is measured. The second scan J2 is the OCT measurement of the second cross section near the first cross section. The example shown in FIG. 8 alternately performs a single first scan (i.e., a single B scan of the first cross section) and a single second scan (i.e., a single B scan of the second cross section). Through such scans, the followings are acquired: the pair of data $[J1, J2]_1$, acquired through the first scan of the first time and the second scan of the first time; the pair of data $[J1, J2]_2$, acquired through the first scan of the second time and the second scan of the second time; . . . ; the pair of data $[J1, J2]_n$, acquired through the first scan of the n-th time and the second scan of the n-th time. The data pairs $[J1, J2]_i$ (i=1 to n) correspond to the times $t_i$ (i=1 to n), respectively. Any time point during the OCT measurement to acquire the data pair $[J1, J2]_i$ (i=1 to n) is assigned to the time $t_i$ (i=1 to n). It is possible to alternately perform one or more times of the first scan and one or more times of the second scan.

The image forming unit 220 in step 860 (S6) forms images based on the data acquired in step 850 (S5). In the present operation example, based on each of the data pairs $[J1, J2]_i$ (i=1 to n), the cross sectional image forming unit 221 forms the first cross sectional image $T1_i$ (i=1 to n) rendering the first cross section and the second cross sectional image $T2_i$ (i=1 to n) rendering the second cross section. The first cross sectional image $T1_i$ and the second cross sectional image $T2_i$ (i=1 to n) correspond to the time $t_i$ (i=1 to n).

In addition, based on the data $[J1]_i$ (i=1 to n−1) on the first cross section included in the data pair $[J1, J2]_i$ (i=1 to n−1) and the data $[J1]_{i+1}$ (i=1 to n−1) on the first cross section included in the nest data pair $[J1, J2]_{i+1}$ (i=1 to n−1), the phase image forming unit 222 forms the phase image $P_i$ (i=1 to n−1) rendering the first cross section. The phase image $P_i$ (i=1 to n−1) correspond to the times $t_i$ (i=1 to n−1). In the same manner, phase images of the second cross section can be formed based on the data $[J2]_i$ (i=1 to n) on the second cross section.

The present operation example does not create the phase image $P_n$ corresponding to the time $t_n$; however, the phase image $P_n$ can be created by performing the n+1-th OCT measurement of the first cross section. Alternatively, the phase image $P_n$ may be a copy of the phase image $P_{n-1}$. In another example, the first cross sectional image $T1_n$ and the second cross sectional image $T2_n$ both corresponding to the time $t_n$ are not formed. Another example may form one or more representative pairs of the first cross sectional image and the second cross sectional image based on any one or more representative data pairs among the data pairs $[J1, J2]_i$ (i=1 to n).

At step 870 (S7), the blood vessel region specification unit 231 specifies a blood vessel region corresponding to the interested blood vessel for each of the first cross sectional image $T1_i$, the second cross sectional image $T2_i$, and the phase image $P_i$.

At step 880 (S8), the gradient calculation unit 232 calculates the gradient of the interested blood vessel at the first cross section based on the blood vessel regions specified in step 870 (S7) and the distance between the first cross section and the second cross section (i.e., cross section interval). As a specific example, based on the cross section interval and two blood vessel regions specified from the first cross sectional image $T1_i$ and the second cross sectional image $T2_i$ (i=1 to n) at the time $t_i$ (i=1 to n), the gradient calculation unit 232 can calculate the gradient $A_i$ (i=1 to n) of the interested blood vessel at the time $t_i$ (i=1 to n). Here, in place of the first cross sectional image $T1_i$, a blood vessel region specified from the phase image $P_i$ may be used. Instead of calculating the gradient $A_i$ (i=1 to n) corresponding to the time $t_i$ (i=1 to n), one or more representative gradient values may be determined. For example, it is possible to divide the period $t_i$ to $t_n$ into one or more partial periods, calculate a statistic (e.g., mean value or median) from a plurality of gradients $A_i$ corresponding to each of the partial periods, and set the calculated statistic to the gradient of the interested blood vessel at the corresponding partial period.

Based on the chronological change in the phase difference obtained as the phase images $P_i$ (i=1 to n−1) and the gradients $A_i$ (i=1 to n) of the interested blood vessel calculated in step 880 (S8), the blood flow velocity calculation unit 234 in step 890 (S9) calculates the blood flow velocity $v_i$ (i=1 to n) at the first cross section for the blood flowing through the interested blood vessel. The blood flow velocity values $v_i$ (i=1 to n) correspond to the times $t_i$ (i=1 to n), respectively. When the phase image $P_n$ is not formed, the blood flow velocity $v_n$ may not been calculated.

Based on the first cross sectional images $T1_i$ (i=1 to n) or the phase images $P_i$ (i=1 to n−1), the blood vessel diameter calculation unit 235 in step 900 (S10) calculates the diameter $w_i$ (i=1 to n) of the interested blood vessel at the first cross section. In place of determining the blood vessel diameters $w_i$ (i=1 to n) corresponding to the times $t_i$ (i=1 to n), one or more representative blood vessel diameters may be determined. The blood vessel diameter may be calculated by analyzing fundus images instead of the first cross sectional images. The blood vessel diameter at the second cross section may be determined in addition to the blood vessel diameter at the first cross section. In such a case, the blood vessel diameter at the first cross section and the blood vessel diameter at the second cross section are different from one another, in general.

Based on the blood flow velocity determined in step 890 (S9) and the blood vessel diameter determined in step 900 (S10), the blood flow amount calculation unit 236 in step 910 (S11) calculates the flow amount Q (μL/min) of the blood that flows through the interested blood vessel.

The main controller 211 displays blood flow information including the blood flow velocity $v_i$ calculated in step 890 (S9), the blood vessel diameter $w_i$ calculated in step 900 (S10), the blood flow amount Q calculated in step 910 (S11), etc. on the display unit 241 in step 920 (S12). In addition, the main controller 211 associates the blood flow information with the patient ID input in step 810 (S1), and stores it in the storage unit 212. This terminates the processing of the present operation example.

Effects

Effects of the blood flow measurement apparatus of the embodiment will be described.

The blood flow measurement apparatus of the embodiment includes a scanner, an image forming unit, a blood vessel region specification unit, a gradient calculation unit, and a blood flow information generation unit.

The scanner is configured to alternately perform first scan that scans a first cross section that intersects an interested blood vessel of a living body and second scan that scans a second cross section that intersects the interested blood vessel using optical coherence tomography. In the present embodiment, the scanner includes at least the optical system for performing OCT measurement. For example, the optical path of the measurement light LS shown in FIG. 1 and the optical system shown in FIG. 2 are included.

The image forming unit is configured to form one or more images of the first cross section at least including a phase image that represents chronological change in phase difference in the first cross section based on data acquired through the first scan. An image of the first cross section other than the phase image may be any image formed from data acquired through OCT. An example of the image of the first cross section other than the phase image is a first cross sectional image representing (the chronological change of) the morphology of the first cross section. In addition, the image forming unit is configured to form an image of the second cross section based on data acquired through the second scan. An example of the image of the second cross section is a second cross sectional image representing (the chronological change of) the morphology of the second cross section. In the present embodiment, the image forming unit 220 functions as the image forming unit.

The blood vessel region specification unit is configured to specify a first blood vessel region corresponding to the interested blood vessel in the image of the first cross section formed by the image forming unit. In addition, the blood vessel region specification unit is configured to specify a second blood vessel region corresponding to the interested blood vessel in the image of the second cross section. In the present embodiment, the blood vessel region specification unit 231 functions as the blood vessel region specification unit.

The gradient calculation unit is configured to calculate the gradient of the interested blood vessel at the first cross section based on the first blood vessel region and the second blood vessel region specified by the blood vessel region specification unit. In the present embodiment, the gradient calculation unit 232 functions as the gradient calculation unit.

The blood flow information generation unit is configured to generate blood flow information on the interested blood vessel based on the phase image formed by the image forming unit and the gradient of the interested blood vessel calculated by the gradient calculation unit. In the present embodiment, the blood flow information generation unit 233 functions as the blood flow information generation unit.

The blood flow measurement apparatus thus configured is capable of measuring two cross sections alternately, determining the gradient of the blood vessel based on the data acquired thereby, and obtaining the blood flow information. On the other hand, according to conventional techniques, blood flow information is acquired by individually performing the measurement for estimating the gradient of the blood vessel and Doppler OCT, or by applying Doppler OCT to two cross sections. Accordingly, the present embodiment is capable of carrying out blood flow measurement in a shorter time compared to the conventional techniques. In addition, since the present embodiment employs the configuration of alternately performing the first scan and the second scan, that is, the configuration of performing the first scan and the second scan in parallel, there is (almost) no negative effect of the movement of the object. Thus, highly reliable blood flow information can be obtained.

In the embodiment, the gradient calculation unit may be configured to determine the chronological change in the gradient ($A_i$ (i=1 to n)) of the interested blood vessel. In addition, the blood flow information generation unit may be configured to generate blood flow information for the timing (time $t_i$) based on one image frame ($P_i$) of the phase image and the gradient ($A_i$) at timing (time $t_i$) corresponding to the image frame ($P_i$). The blood flow information includes, for example, at least one of the blood flow velocity $v_i$, the blood vessel diameter $w_i$, and the blood flow amount Q.

More specifically, based on data ($[J1]_i$) acquired through the first scan performed at one timing (time $t_i$) and data (e.g., $[J2]_{i-1}$ or $[J2]_i$) acquired through the second scan performed immediately before or immediately after this first scan, the gradient calculation unit may calculate the gradient ($A_i$) of the interested blood vessel for the one timing (time $t_i$). In addition, based on an image frame ($P_i$) of the phase image corresponding to the one timing (time $t_i$) and the gradient ($A_i$) of the interested blood vessel for the one timing (time $t_i$), the blood flow information generation unit may generate blood flow information for the one timing (time $t_i$).

With such a configuration, even when the gradient of the interested blood vessel varies due to the movement of the living body etc., the blood flow information can be obtained for any timing from the calculation result of the gradient at the timing. Thus, it is possible to acquire blood flow information with higher reliability. This effect can be achieved by the alternate execution of the first scan and the second scan.

In the embodiment, the blood flow information generation unit may include a blood flow velocity calculation unit (234) configured to determine chronological change in the blood flow velocity $v_i$ (i=1 to n) at the first cross section for blood flowing through the interested blood vessel based on the phase image and the gradient of the interested blood vessel. With such a configuration, the blood flow information that includes at least the blood flow velocity can be obtained.

In the embodiment, the blood flow information generation unit may include a blood vessel diameter calculation unit (235) and a blood flow amount calculation unit (236). The blood vessel diameter calculation unit is configured to calculate the diameter ($w_i$) of the interested blood vessel at the first cross section based on the first blood vessel region specified by the blood vessel region specification unit. The blood flow amount calculation unit is configured to calculate the blood flow amount (Q) of the blood flowing through the interested blood vessel based on the chronological change in the blood flow velocity $v_i$ (i=1 to n) and the diameter ($w_i$) of the interested blood vessel. With such a configuration, the blood flow information that includes at least the blood flow amount can be obtained.

In addition, the blood vessel diameter calculation unit may determine the chronological change in the diameter $w_i$ (i=1 to n) of the interested blood vessel. In this case, the blood flow amount calculation unit may calculate the flow amount (Q) of the blood flowing through the interested blood vessel based on the chronological change in the blood flow velocity $v_i$ (i=1 to n) and the chronological change in the diameter $w_i$ (i=1 to n) of the interested blood vessel. With such a configuration, it is possible to improve the reliability of the blood flow amount calculated.

The number of the interested blood vessel is not limited to one, and two or more interested blood vessels can be considered. Two or more interested blood vessels can be rendered in a pair of the first cross section and the second cross section. When considering two or more interested blood vessels, the processing described in the present embodiment is applied to each of the interested blood vessels. With this, blood flow information (the gradient of the blood vessel, the blood vessel diameter, the blood flow velocity, the blood flow amount, etc.) for each of the interested blood vessels can be obtained.

Modification Examples

The configurations described above are merely examples for implementing the present invention. Therefore, it is possible to make arbitrary modification (omission, replacement, addition, etc.) within the scope of the present invention.

A modification example of method of calculating blood flow amount will be described. In the present modification example, the blood flow velocity calculation unit 234 generates information (blood flow velocity variation information) that represents chronological change in the blood flow velocity for each pixel included in the blood vessel region in the phase image. The generation of the blood flow velocity variation information may include: a position matching between a plurality of phase images arranged in time series order in a pixel-to-pixel manner (i.e., for each pixel position); and a process of generating the blood flow velocity variation information based on the plurality of pixels arranged in time series order corresponding to each pixel position. With such processing, the blood flow velocity can be determined for each position in the blood vessel region of the first cross section.

The blood flow amount calculation unit 236 calculates the blood flow amount for each pixel through time integration of the blood flow velocity variation information for the pixel included in the blood vessel region. With this processing, the blood flow amount can be determined for each point in the blood vessel region in the first cross section.

Further, the blood flow amount calculation unit 236 can calculate the flow amount of the blood flowing through the interested blood vessel by adding the blood flow amounts for these pixels. With this processing, the blood flow amounts for the plurality of pixels obtained in the prior stage are added together to determine the total amount of the blood that flows within the blood vessel region of the first cross section.

In the above embodiment, the optical path length difference between the optical path of the measurement light LS and the optical path of the reference light LR is changed by varying the position of the optical path length changer 41; however, a method of changing the optical path length difference is not limited to this. For example, it is possible to change the optical path length difference by providing a reflection mirror (i.e., reference mirror) in the optical path of the reference light, and moving the reference mirror in the advancing direction of the reference light to change the optical path length of the reference light. Alternatively, the optical path length difference may be changed by moving the fundus camera unit 2 and/or the OCT unit 100 with respect to the eye E to change the optical path length of the measurement light LS. In another example, if an object to be measured is not a site of a living body or the like, it can be configured to change the optical path length difference by moving the object in the depth direction (z direction).

The invention claimed is:

1. A blood flow measurement apparatus comprising:
   a scanner configured to perform a plurality of first B scans using optical coherence tomography (OCT) and a plurality of second B scans using OCT in such a manner that one or more of the plurality of first B scans are performed between two of the plurality of second B scans, and that one or more of the plurality of second B scans are performed between two of the plurality of first B scans, and wherein each of the plurality of first B scans is performed on a first cross section that intersects an interested blood vessel of a living body and each of the plurality of second B scans is performed on a second cross section that is different from the first cross section and intersects the interested blood vessel;
   an image forming unit configured to form one or more images of the first cross section including a phase image that represents chronological change in phase difference in the first cross section based on data acquired from the first cross section, and form one or more images of the second cross section based on data acquired from the second cross section;
   a blood vessel region specification unit configured to specify a first blood vessel region corresponding to the interested blood vessel in any of the one or more first cross sectional images and the phase image of the first cross section, and specify a second blood vessel region corresponding to the interested blood vessel in the one or more second cross sectional images of the second cross section;
   a gradient calculation unit configured to calculate a gradient of the interested blood vessel at the first cross section based on the first blood vessel region and the second blood vessel region; and
   a blood flow information generation unit configured to generate blood flow information on the interested blood vessel based on the phase image and the gradient of the interested blood vessel.

2. The blood flow measurement apparatus of claim 1, wherein the image forming unit is further configured to form a cross sectional image that represents chronological change in morphology in the first cross section based on the data acquired from the first cross section.

3. The blood flow measurement apparatus of claim 1, wherein
   the gradient calculation unit is further configured to determine chronological change in the gradient of the interested blood vessel, and
   based on an image frame of the phase image and a gradient at timing corresponding to the image frame, the blood flow information generation unit is further configured to generate blood flow information for the timing.

4. The blood flow measurement apparatus of claim 3, wherein
   based on data acquired, at a specific measurement time point, through the plurality of first B scans and data acquired through the plurality of second B scans, the gradient calculation unit is further configured to calculate a gradient of the interested blood vessel, and
   based on an image frame of the phase image and the gradient of the interested blood vessel, the blood flow information generation unit is further configured to generate blood flow information.

5. The blood flow measurement apparatus of claim 1, wherein the blood flow information generation unit comprises a blood flow velocity calculation unit configured to determine chronological change in blood flow velocity at the first cross section for blood flowing through the interested blood vessel based on the phase image and the gradient of the interested blood vessel.

6. The blood flow measurement apparatus of claim 5, wherein the blood flow information generation unit comprises:
   a blood vessel diameter calculation unit configured to calculate diameter of the interested blood vessel at the first cross section based on the first blood vessel region specified by the blood vessel region specification unit; and
   a blood flow amount calculation unit configured to calculate flow amount of blood flowing through the interested blood vessel based on the chronological change in the blood flow velocity and the diameter of the interested blood vessel.

7. The blood flow measurement apparatus of claim 6, wherein
   the blood vessel diameter calculation unit is further configured to determine chronological change in the diameter of the interested blood vessel, and
   the blood flow amount calculation unit is further configured to calculate the flow amount based on the chronological change in the blood flow velocity and the chronological change in the diameter of the interested blood vessel.

8. The blood flow measurement apparatus of claim 2, wherein
   the gradient calculation unit is further configured to determine chronological change in the gradient of the interested blood vessel, and
   based on an image frame of the phase image and a gradient at timing corresponding to the image frame, the blood flow information generation unit is further configured to generate blood flow information for the timing.

9. The blood flow measurement apparatus of claim 2, wherein the blood flow information generation unit comprises a blood flow velocity calculation unit configured to determine chronological change in blood flow velocity at the first cross section for blood flowing through the interested blood vessel based on the phase image and the gradient of the interested blood vessel.

10. The blood flow measurement apparatus of claim 3, wherein the blood flow information generation unit comprises a blood flow velocity calculation unit configured to determine chronological change in blood flow velocity at the first cross section for blood flowing through the interested blood vessel based on the phase image and the gradient of the interested blood vessel.

11. The blood flow measurement apparatus of claim 4, wherein the blood flow information generation unit comprises a blood flow velocity calculation unit configured to determine chronological change in blood flow velocity at the first cross section for blood flowing through the interested blood vessel based on the phase image and the gradient of the interested blood vessel.

12. A method of acquiring blood flow information on an interested blood vessel of a living body, the method comprising:

performing a plurality of first B scans using optical coherence tomography (OCT) and a plurality of second B scans using OCT in such a manner that one or more of the plurality of first B scans are performed between two of the plurality of second B scans, and that one or more of the plurality of second B scans are performed between two of the plurality of first B scans, and wherein each of the plurality of first B scans is performed on a first cross section that intersects the interested blood vessel and each of the plurality of second B scans is performed on a second cross section that is different from the first cross section and intersects the interested blood vessel;

forming one or more images of the first cross section including a phase image that represents chronological change in phase difference in the first cross section based on data acquired from the first cross section, and forming one or more images of the second cross section based on data acquired from the second cross section;

specifying a first blood vessel region corresponding to the interested blood vessel in any of the one or more first cross sectional images and the phase image of the first cross section;

specifying a second blood vessel region corresponding to the interested blood vessel in the one or more second cross sectional images of the second cross section;

calculating a gradient of the interested blood vessel at the first cross section based on the first blood vessel region and the second blood vessel region; and generating blood flow information on the interested blood vessel based on the phase image and the gradient of the interested blood vessel.

* * * * *